(12) United States Patent
Dasbach

(10) Patent No.: US 12,303,670 B2
(45) Date of Patent: May 20, 2025

(54) DRUG DELIVERY DEVICE

(71) Applicant: Sanofi-Aventis Deutschland GMBH, Frankfurt am Main (DE)

(72) Inventor: Uwe Dasbach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 102 days.

(21) Appl. No.: 18/174,371

(22) Filed: Feb. 24, 2023

(65) Prior Publication Data
US 2024/0017009 A1    Jan. 18, 2024

Related U.S. Application Data

(62) Division of application No. 16/317,008, filed as application No. PCT/EP2017/065895 on Jun. 27, 2017, now Pat. No. 11,617,834.

(30) Foreign Application Priority Data

Jul. 13, 2016    (EP) .................... 16179240

(51) Int. Cl.
*A61M 5/24* (2006.01)
*A61J 1/06* (2006.01)
(Continued)

(52) U.S. Cl.
CPC ............... *A61M 5/24* (2013.01); *A61J 1/065* (2013.01); *A61M 5/002* (2013.01); *A61M 5/28* (2013.01);
(Continued)

(58) Field of Classification Search
CPC .. A61M 5/24; A61M 5/28; A61M 2005/3126; B65D 25/56; A61J 2205/30; G09F 3/10; G09F 2003/0273
See application file for complete search history.

(56) References Cited

U.S. PATENT DOCUMENTS 5,279,586 A    1/1994    Balkwill
5,716,317 A *  2/1998    Okano ................ A61M 5/1785
                                                        600/4

(Continued)

FOREIGN PATENT DOCUMENTS

CN    102711711    10/2012
EP    0554995      8/1993
(Continued)

OTHER PUBLICATIONS

International Preliminary Report on Patentability in International Application No. PCT/EP2017/065895, dated Jan. 15, 2019, 9 pages.
(Continued)

*Primary Examiner* — Bradley J Osinski
(74) *Attorney, Agent, or Firm* — Bond, Schoeneck & King, PLLC

(57) ABSTRACT

The present disclosure relates to a drug delivery device, comprising a shell adapted to contain one of a plurality of medicament containers prefilled with different deliverable volumes of a medicament. The shell is transparent at least in an area adapted to contain the medicament container, and a label adapted to be arranged on the shell. The label comprises a foil having a first surface and a second surface, which is adapted to be connected to the shell. At least one cutout or transparent area is arranged in the foil adapted to be placed on the shell such that a medicament container arrangeable or arranged within the shell is visible through the cutout or transparent area. The cutout or transparent area exhibits a size adapted to allow inspection of the deliverable volume of medicament within the medicament container when the label is applied to the shell.

20 Claims, 4 Drawing Sheets

(51) Int. Cl.
*A61M 5/00* (2006.01)
*A61M 5/28* (2006.01)
*A61M 5/31* (2006.01)
*B65D 25/56* (2006.01)
*G09F 3/02* (2006.01)
*G09F 3/10* (2006.01)

(52) U.S. Cl.
CPC ............... *B65D 25/56* (2013.01); *G09F 3/02* (2013.01); *A61J 2205/30* (2013.01); *A61M 2005/3126* (2013.01); *G09F 2003/0273* (2013.01); *G09F 3/10* (2013.01)

(56) References Cited

U.S. PATENT DOCUMENTS

| | | | |
|---|---|---|---|
| 5,720,729 A * | 2/1998 | Kriesel | A61M 5/1409 604/132 |
| 2003/0134073 A1 | 7/2003 | Sellars | |
| 2008/0188814 A1* | 8/2008 | Lavi-Loebl | A61M 5/28 604/189 |
| 2008/0195077 A1 | 8/2008 | Anatrini | |
| 2012/0279103 A1 | 11/2012 | Seidl | |
| 2019/0290850 A1 | 9/2019 | Dasbach | |

FOREIGN PATENT DOCUMENTS

| | | |
|---|---|---|
| EP | 0554996 | 8/1993 |
| EP | 1044698 | 10/2000 |
| EP | 1557188 | 7/2005 |
| EP | 1946787 | 7/2008 |
| EP | 2654032 | 10/2013 |
| JP | S59-15066 | 1/1984 |
| JP | H05-337179 | 12/1993 |
| JP | 2002-095745 | 4/2002 |
| JP | 2002-541932 | 12/2002 |
| JP | 2006-220695 | 8/2006 |
| JP | 2007-190128 | 8/2007 |
| JP | 2007-195711 | 8/2007 |
| JP | 3150720 | 5/2009 |
| JP | 2013-517816 | 5/2013 |
| JP | 3187729 | 12/2013 |
| WO | WO 2000/062848 | 10/2000 |
| WO | WO 2010/043875 | 4/2010 |
| WO | WO 2011/089204 | 7/2011 |

OTHER PUBLICATIONS

International Search Report and Written Opinion in International Application No. PCT/EP2017/065895, dated Aug. 16, 2017, 13 pages.

Third Party Observation in EP Patent Application No. 17735451.1, dated May 29, 2019, 33 pages.

* cited by examiner

DRUG DELIVERY DEVICE

CROSS REFERENCE TO RELATED APPLICATIONS

The present application is a divisional of U.S. patent application Ser. No. 16/317,008, filed Jan. 10, 2019, which is the national stage entry of International Patent Application No. PCT/EP2017/065895, filed on Jun. 27, 2017, and claims priority to Application No. EP 16179240.3, filed on Jul. 13, 2016, the disclosures of which are incorporated herein by reference.

TECHNICAL FIELD

The disclosure generally relates to a label for a drug delivery device, a drug delivery device having such a label, a kit for assembling a drug delivery device, and a method of assembling a drug delivery device.

BACKGROUND

Drug delivery devices such as auto-injectors typically allow for visually inspecting the deliverable volume of drug, e.g. through a window provided in an outer shell of the drug delivery device.

SUMMARY

According to the present disclosure, a drug delivery device comprises:
- a shell adapted to contain one of a plurality of medicament containers prefilled with different deliverable volumes of a medicament, wherein the shell is transparent at least in an area adapted to contain the medicament container, and
- a label adapted to be arranged on the shell, wherein the label comprises a foil having a first surface and a second surface which is adapted to be connected to the shell, wherein at least one cutout or transparent area is arranged in the foil adapted to be placed on the shell such that a medicament container arrangeable or arranged within the shell is visible through the cutout or transparent area, wherein the cutout or transparent area exhibits a size adapted to allow inspection of the deliverable volume of medicament, e.g. the complete deliverable volume or a part thereof, within the medicament container when the label is applied to the shell.

Selecting a label with a cutout or transparent area whose size, e.g. length and/or width, corresponds with the deliverable volume of the medicament container, allows for applying medicament containers with different deliverable volumes within the same shell of the drug delivery device without having to adapt the shell or selecting shells with different window sizes for medicament containers with different deliverable volumes which requires different moulding tools. Adapting the label instead provides a much cheaper solution.

The medicament container may for example, be a syringe with a fixed injection needle or cartridge having an end adapted to be connected to a removable injection needle.

The shell may be a substantially tubular part.

In an exemplary embodiment, the label is selected such that the size of the cutout or transparent area corresponds to one of a plurality of different deliverable volumes of medicament within a respective medicament container, e.g. 0.3 ml, 0.5 ml and 1.0 ml. The smaller the volume, the smaller the cutout or transparent area of the label can be made.

In an exemplary embodiment, the foil is opaque except for the cutout or transparent area in order to obscure interiors of the drug delivery device outside the deliverable volume. The external design of the drug delivery device may thus be adapted for different products, e.g. by colouring the opaque parts of the label and/or printing further relevant information thereon while the internals of the shell aside from the part of the medicament container holding the deliverable volume are hidden from view.

In an exemplary embodiment, the cutout or transparent area is pointed to indicate a distal direction when applied to the shell of the drug delivery device. The distal direction in the context of the present disclosure is the direction of an end of the drug delivery device, which is intended to be closest to an injection site, e.g. a patient's skin, during delivery of the medicament. Giving the cutout or transparent area a pointed appearance allows the user to easily identify which end of the drug delivery device has to be placed against the injection site.

In an exemplary embodiment, at least one arrow is printed on the first surface to indicate a distal direction when applied to the shell of the drug delivery device. The arrow allows the user to easily identify which end of the drug delivery device has to be placed against the injection site. In an exemplary embodiment, the arrow is printed between two cutouts or transparent areas.

In an exemplary embodiment a line grid and/or a scale is printed on the foil adjacent the cutout or transparent area. This allows the user to determine the progress of the drug delivery, e.g. by observing a position of a stopper within the medicament container with respect to the line grid or scale.

In an exemplary embodiment, the second surface is coated with an adhesive.

In an exemplary embodiment, an outer surface of the shell is coated with an adhesive. This allows applying a non-adhesive label.

The shell only has to be transparent in an area adapted to contain the medicament container, in particular the one with the greatest deliverable volume. In another exemplary embodiment, the entire shell may be transparent.

According to an aspect of the present disclosure a kit for assembling a drug delivery device is provided. the kit comprises:
- a shell adapted to contain one of a plurality of medicament containers prefilled with different deliverable volumes of a medicament, wherein the shell is transparent at least in an area adapted to contain the medicament container, and
- a plurality of labels adapted to be arranged on the shell, wherein each one of the plurality of labels comprises a foil having a first surface and a second surface which is adapted to be connected to the shell, wherein at least one cutout or transparent area is arranged in the foil of each one of the plurality of labels, the at least one cutout or transparent area being adapted to be placed on the shell such that a medicament container arrangeable or arranged within the shell is visible through the cutout or transparent area, wherein the plurality of labels comprises different labels differing in a size of their respective at least one cutout or transparent area to allow inspection of the deliverable volumes of different medicament containers out of the plurality of medicament containers.

Selecting a label with a cutout or transparent area whose size, e.g. length and/or width, corresponds with the deliverable volume of the medicament container allows for applying medicament containers with different deliverable volumes within the same shell of the drug delivery device without having to adapt the shell. Adapting the label instead provides a much cheaper solution.

According to another aspect of the present disclosure, a method of assembling a drug delivery device comprises:
   providing a shell which is transparent at least in an area adapted to contain one of a plurality of medicament containers prefilled with different deliverable volumes of a medicament,
      selecting a medicament container out of the plurality of medicament containers to be inserted in the shell and prefilled with a defined deliverable volume of a medicament,
      selecting a label out of a plurality of labels, each one having at least one cutout or transparent area exhibiting a size adapted to allow inspection of the deliverable volume of medicament within at least one out of plurality of medicament containers, wherein the label is selected such that the size of its at least one cutout or transparent area corresponds to the selected medicament container, and
      applying the label onto the shell to allow inspection of the deliverable volume of the medicament within the selected medicament container through the at least one cutout or transparent area.

In an exemplary embodiment, the cutout or transparent area is pointed, wherein the label is applied to the shell such that the pointed cutout or transparent area indicates a distal direction.

In an exemplary embodiment, at least one arrow is printed on the first surface, wherein the label is applied to the shell such that the arrow indicates a distal direction.

Selecting a label with a cutout or transparent area whose size, e.g. length and/or width, corresponds with the deliverable volume of the medicament container allows for applying medicament containers with different deliverable volumes within the same shell of the drug delivery device without having to adapt the shell. Adapting the label instead provides a much cheaper solution. The shell only has to be transparent in an area adapted to contain the medicament container, in particular the one with the greatest deliverable volume. In another exemplary embodiment, the entire shell may be transparent.

According to yet another aspect of the present disclosure, a label for a drug delivery device is provided, the label comprising a foil having a first surface and a second surface which is adapted to be adhesively connected to a shell of the drug delivery device, wherein at least one cutout or transparent area is arranged in the foil adapted to be placed on the shell such that a medicament container arranged within the shell is visible through the cutout or transparent area, wherein a size of the cutout or transparent area is selected to allow inspection of the deliverable volume of medicament within the medicament container when the label is applied to the shell.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
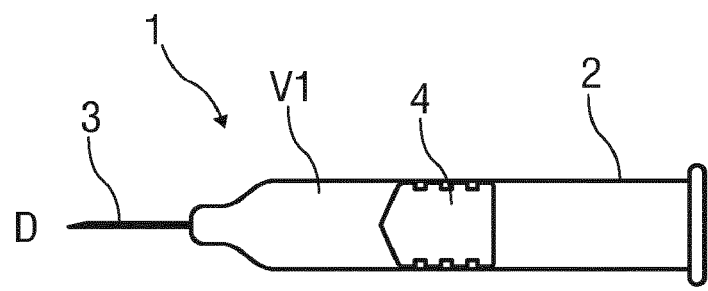
FIG. 1 is a schematic view of a medicament container adapted to hold a first deliverable volume of a medicament.

FIG. 1 is a schematic view of a medicament container 1 adapted to hold a first deliverable volume V1 of a medicament. The medicament container 1 may comprise a barrel 2 defining a substantially cylindrical cavity within for receiving the first deliverable volume V1 of a medicament. A distal end of the barrel 2 is closed and an injection needle 3 is arranged within the distal end to allow injection of the medicament through the injection needle 3. In other, non-illustrated embodiments, the distal end of the barrel 2 does not have a fixed injection needle 3 but may be adapted to releasably mount a removable injection needle. A stopper 4 is arranged within the barrel 2 to seal it proximally and to allow displacing the medicament when the stopper 4 is moved in a distal direction D. The internal diameter of the barrel 2 and an initial position of the stopper 4 define the first deliverable volume V1. In an exemplary embodiment, the first deliverable volume may be 0.3 ml.

Figure 2:
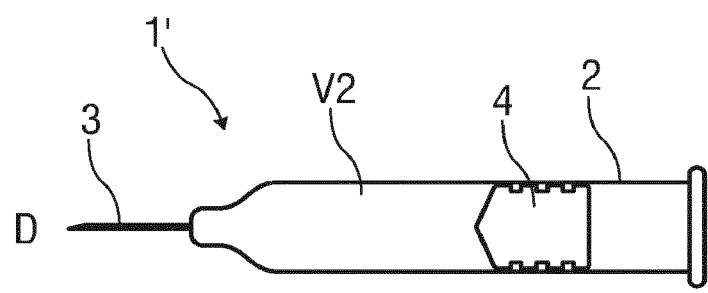
FIG. 2 is a schematic view of a medicament container adapted to hold a second deliverable volume of a medicament.

FIG. 2 is a schematic view of a medicament container 1' adapted to hold a second deliverable volume V2 of a medicament. The medicament container 1' may be identical with the medicament container 1 of FIG. 1. However, the initial position of the stopper 4 is more proximal than in FIG. 1 so that the second deliverable volume V2 is greater than the first deliverable volume V1. In an exemplary embodiment, the second deliverable volume may be 0.5 ml.

Figure 3:
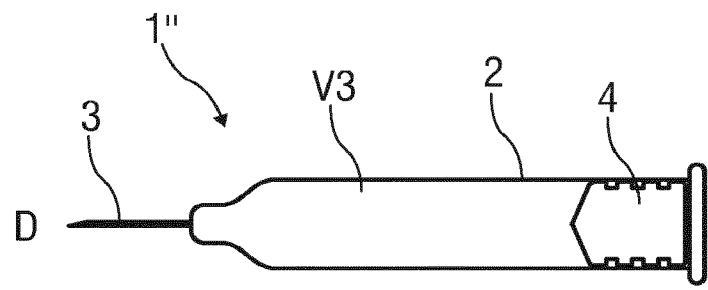
FIG. 3 is a schematic view of a medicament container adapted to hold a third deliverable volume of a medicament.

FIG. 3 is a schematic view of a medicament container 1" adapted to hold a third deliverable volume V3 of a medicament. The medicament container 1" may be identical with the medicament containers 1, 1' of FIGS. 1 and 2. However, the initial position of the stopper 4 is more proximal than in FIG. 2 so that the third deliverable volume V3 is greater than the second deliverable volume V2. In an exemplary embodiment, the third deliverable volume may be 1.0 ml.

The skilled person will readily understand that medicament containers 1, 1', 1" with other deliverable volumes may be provided.

Figure 4:
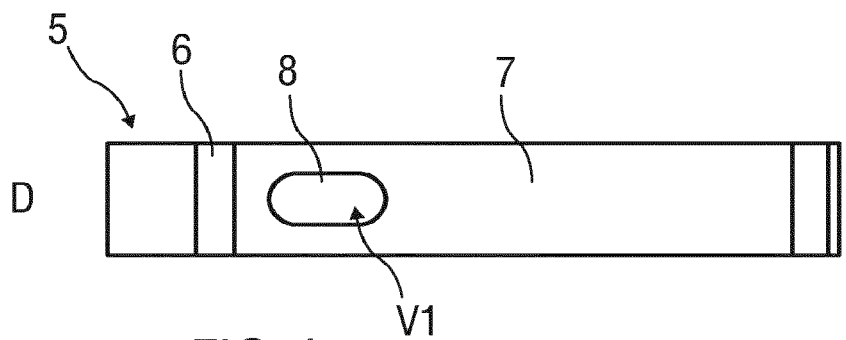
FIG. 4 is a schematic view of a drug delivery device comprising a shell and a label with a cutout for allowing visual inspection of the first deliverable volume of the medicament within the medicament container of FIG. 1 arranged within the shell.

FIG. 4 is a schematic view of a drug delivery device 5 comprising a shell 6 and a label 7 with a cutout 8 or transparent area for allowing visual inspection of the first deliverable volume V1 of the medicament within the medicament container 1 of FIG. 1 arranged within the shell 6.

The shell 6 may be adapted to contain one of a plurality of medicament containers 1, 1', 1" prefilled with different deliverable volumes V1, V2, V3 of medicament, wherein the shell 6 is transparent at least in an area adapted to contain the medicament container 1, 1' 1".

The label 7 comprises a foil having a first surface and a second surface which is adapted to be adhesively connected to the shell 6. At least one cutout 8 or transparent area is arranged in the foil adapted to be placed on the shell 6 such that the first deliverable volume V1 of the medicament container 1 arranged within the shell 6 is visible through the cutout 8 or transparent area. A size of the cutout 8 or transparent area is selected to allow inspection of the first deliverable volume V1 of medicament within the medicament container 1 when the label 7 is applied to the shell 6 of the drug delivery device 5.

The label 7 is selected depending on the first deliverable volume V1 and adhesively arranged on the shell 6 to allow inspection of the first deliverable volume V1 of medicament within the medicament container 1.

This allows for applying medicament containers 1, 1', 1" with different deliverable volumes V1, V2, V3 within the same shell 6 of the drug delivery device 5 without having to adapt the shell 6. Adapting the label 7 instead provides a much cheaper solution. The shell 6 only has to be transparent in the area adapted to contain the medicament container 1, 1', 1". In particular, this transparent area is great enough to allow inspection of the medicament container 1" with the greatest deliverable volume V3. In another exemplary embodiment, the entire shell 6 may be transparent.

In an exemplary embodiment, the label 7 or foil is opaque except for the cutout 8 or transparent area. The external design of the drug delivery device 5 may thus be adapted for different products, e.g. by colouring the opaque parts of the label 7 and/or printing further relevant information on the first surface while the internals of the shell 6 aside from the part of the medicament container 1 holding the first deliverable volume V1 are hidden from view.

In an exemplary embodiment, the second surface of the label 7 or foil is coated with an adhesive in order to allow gluing the label 7 to the shell 6.

In another exemplary embodiment, an outer surface of the shell 6 is coated with an adhesive. This allows applying a non-adhesive label 7 onto the shell.

Figure 5:
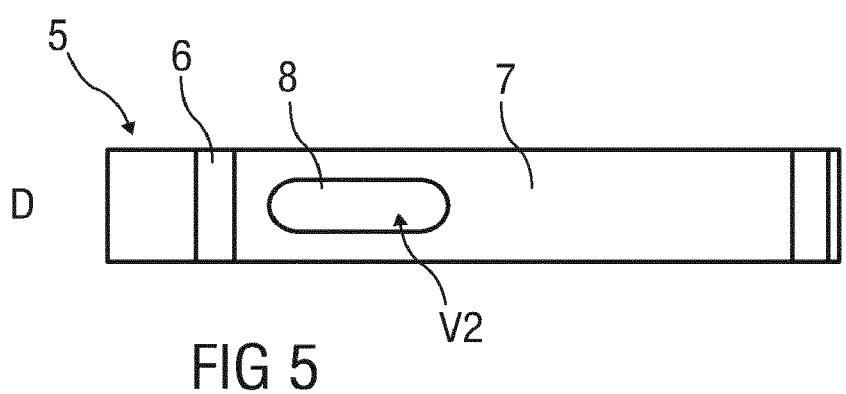
FIG. 5 is a schematic view of a drug delivery device comprising a shell and a label with a cutout for allowing visual inspection of the second deliverable volume of the medicament within the medicament container of FIG. 2 arranged within the shell.

FIG. 5 is a schematic view of a drug delivery device 5 comprising a shell 6 and a label 7 with a cutout 8 for allowing visual inspection of the second deliverable volume V2 of the medicament within the medicament container 1' of FIG. 2 arranged within the shell 6.

The drug delivery device 5 may be identical with the drug delivery device 5 of FIG. 4. In particular, the same shell 6 may be used. The only difference is the label 7, which has a greater cutout 8 or transparent area in order to allow inspection of the greater second deliverable volume V2.

Figure 6:
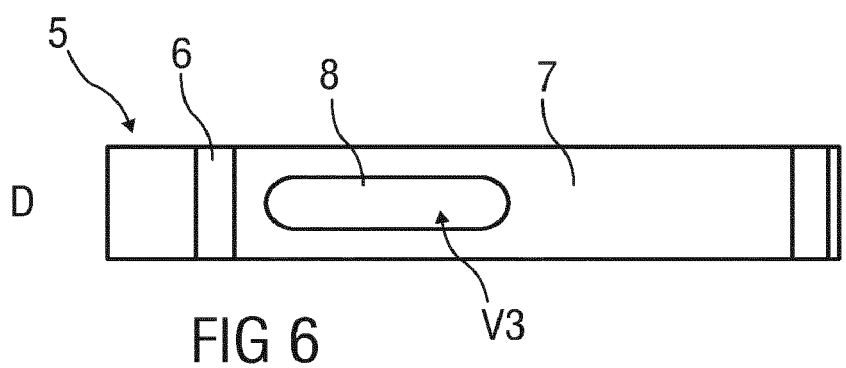
FIG. 6 is a schematic view of a drug delivery device comprising a shell and a label with a cutout for allowing visual inspection of the third deliverable volume of the medicament within the medicament container of FIG. 3 arranged within the shell.

FIG. 6 is a schematic view of a drug delivery device 5 comprising a shell 6 and a label 7 with a cutout 8 for allowing visual inspection of the third deliverable volume V3 of the medicament within the medicament container 1" of FIG. 3 arranged within the shell 6.

The drug delivery device 5 may be identical with the drug delivery devices 5 of FIGS. 4 and 5. In particular, the same shell 6 may be used. The only difference is the label 7, which has an even greater cutout 8 or transparent area in order to allow inspection of the greater third deliverable volume V3.

Figure 7:
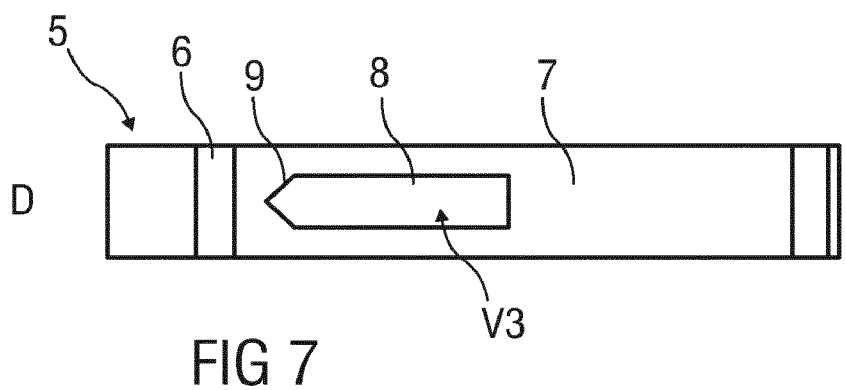
FIG. 7 is a schematic view of a drug delivery device comprising a shell and a label with a cutout for allowing visual inspection of the third deliverable volume of the medicament within the medicament container of FIG. 3 arranged within the shell, wherein the cutout is pointed to indicate a distal direction.

FIG. 7 is a schematic view of a drug delivery device 5 comprising a shell 6 and a label 7 with a cutout 8 for allowing visual inspection of the third deliverable volume V3 of the medicament within the medicament container 1" of FIG. 3 arranged within the shell 6

The drug delivery device 5 may be identical with the drug delivery devices 5 of FIGS. 4 to 6. In particular, the same shell 6 may be used. The only difference is the label 7, which has a cutout 8 or transparent area sized to allow inspection of the third deliverable volume V3 as in FIG. 6 and which additionally has a pointed end 9 to indicate a distal direction D.

Figure 8:
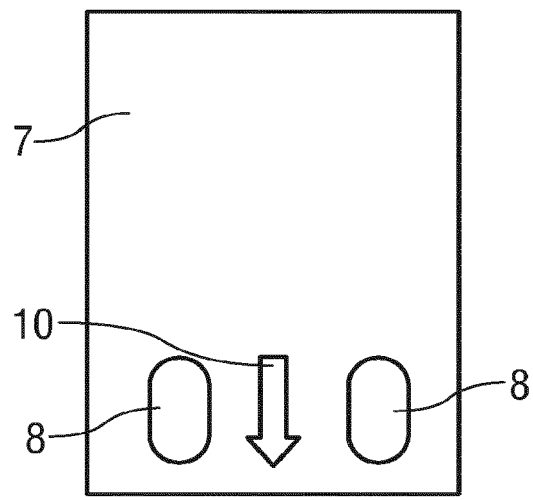
FIG. 8 is a schematic view of the label shown in FIG. 4 with an additional arrow printed on the label to indicate the distal direction.

FIG. 8 is a schematic view of the label 7 shown in FIG. 4 with an additional arrow 10 printed on the first surface of the label 7 to indicate the distal direction D. In the illustrated embodiment, the label 7 comprises two cutouts 8 such that the first deliverable volume V1 can be inspected from two sides when the label 7 is wrapped around the shell 6. In the illustrated embodiment, the arrow 10 is printed between two cutouts 8 or transparent areas. The skilled person will understand that the arrow 10 may be printed on a different part of the label 7.

Figure 9:
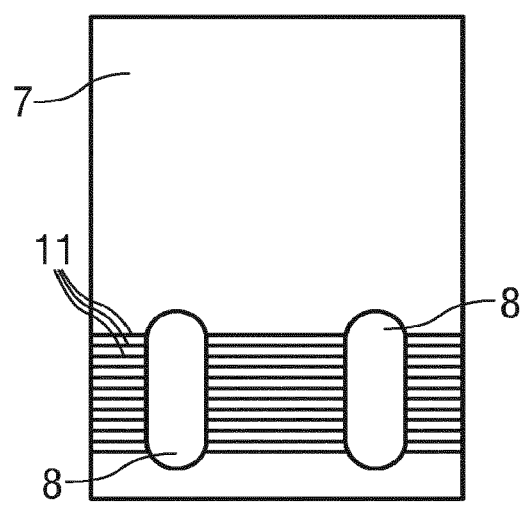
FIG. 9 is a schematic view of the label shown in FIG. 5 with an additional line grid printed on the label.

FIG. 9 is a schematic view of the label 7 shown in FIG. 5 with an additional line grid 11 printed on the label 7 adjacent the cutout 8 or transparent area.

Figure 10:
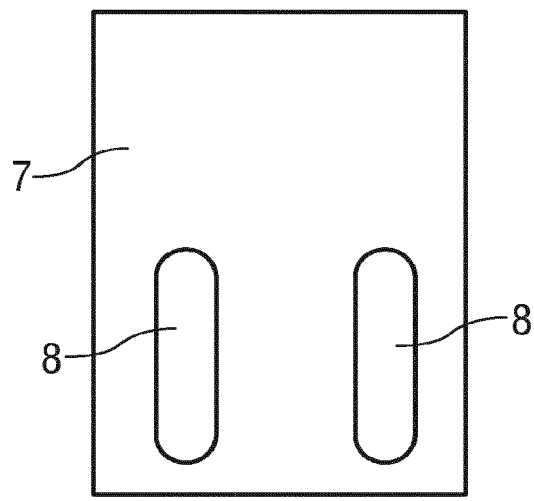
FIG. 10 is a schematic view of the label shown in FIG. 6.

FIG. 10 is a schematic view of the label shown in FIG. 6.

Figure 11:
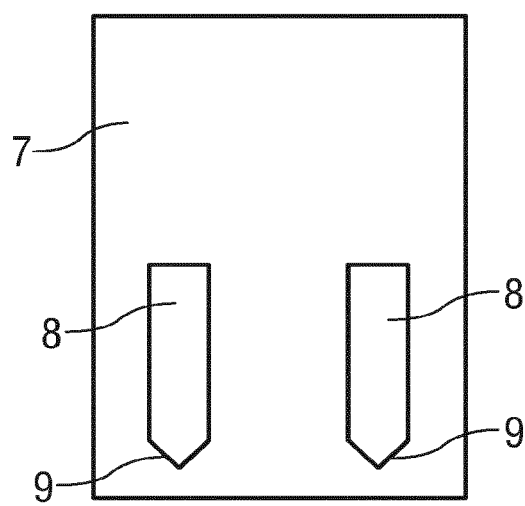
FIG. 11 is a schematic view of the label shown in FIG. 7.

FIG. 11 is a schematic view of the label shown in FIG. 7.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance, which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')$_2$ fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 medicament container
1' medicament container
1" medicament container
2 barrel
3 injection needle
4 stopper
5 drug delivery device
6 shell
7 label
8 cutout
9 pointed end
10 arrow
11 line grid
D distal direction
V1 first deliverable volume
V2 second deliverable volume
V3 third deliverable volume

The invention claimed is:

1. A method of assembling a drug delivery device, the method comprising:
    selecting a medicament container to be inserted in a shell of the drug delivery device, wherein the shell is configured to contain one of a plurality of medicament containers prefilled with different deliverable volumes of a medicament, and wherein at least an area of the shell adapted to contain the selected medicament container is transparent;
    selecting a label out of a plurality of labels, each one having at least one cutout or transparent area sized to allow inspection of a deliverable volume of medicament within the medicament container, wherein the label is selected such that a size of the at least one cutout or transparent area corresponds to a selected medicament container,
    wherein the plurality of labels comprise differently sized cutouts or differently sized transparent areas, and
    wherein selecting the label is dependent on the deliverable volume of medicament within the selected medicament container; and
    applying the label onto the shell to allow inspection of a deliverable volume of medicament within the selected medicament container through the at least one cutout or transparent area.

2. The method according to claim 1, wherein applying the label comprises applying the label to the shell such that a pointed cutout or a pointed transparent area indicates a distal direction.

3. The method according to claim 1, wherein applying the label comprises applying the label to the shell such that an arrow indicates a distal direction, wherein the arrow is printed on a first surface of the label.

4. The method according to claim 3, wherein applying the label comprises applying the label to the shell such that the arrow indicates the distal direction, wherein the arrow is printed between two cutouts or transparent areas.

5. The method according to claim 3, wherein selecting the label comprises selecting the label comprising a foil having a first surface and a second surface, wherein the at least one cutout or transparent area is arranged in the foil.

6. The method according to claim 5, wherein selecting the label comprises selecting the label comprising a line grid and scale printed on the foil adjacent the cutout or transparent area.

7. The method according to claim 5, wherein applying the label comprises connecting an adhesive coating of the second surface of the foil to the shell.

8. The method according to claim 5, wherein applying the label comprises arranging an opaque part of the foil relative to the shell such that interior portions of the drug delivery device outside a deliverable volume are obscured.

9. The method according to claim 8, wherein applying the label comprises arranging an opaque part of the foil relative to the shell such that all interior portions of the drug delivery device outside a deliverable volume are obscured.

10. The method according to claim 8, comprising filling the medicament container with a first deliverable volume that is different from a greater deliverable volume, wherein the medicament container is adapted to store the greater deliverable volume.

11. The method according to claim 10, wherein applying the label comprises covering a part of the medicament container that would be necessary to allow inspection of the greater delivery volume with a portion of the opaque part of the foil, wherein the portion of the opaque part of the foil is arranged proximally of the cutout or of the transparent area.

12. The method according to claim 5, wherein applying the label comprises connecting an adhesive coating of an outer surface of the shell to the foil.

13. The method of claim 3, comprising selecting a shell that is substantially transparent.

14. The method according to claim 1, wherein a difference between labels of the plurality of labels is that the cutouts or transparent areas are differently seized.

15. The method according to claim 14, wherein the labels of the plurality of labels are different in the lengths of the cutouts or transparent areas.

16. The method according to claim 15, wherein the labels of the plurality of labels are different only in the lengths of the cutouts or transparent areas.

17. The method according to claim 1, wherein the deliverable volume is defined by the initial position of a stopper within the medicament container.

18. The method according to claim 17, wherein the deliverable volume is defined by the initial position of a stopper within the medicament container and by an internal diameter of medicament container.

19. A method of assembling a drug delivery device, the method comprising:
   selecting a medicament container to be inserted in a shell;
   selecting a label out of a plurality of labels, each one having at least one cutout or transparent area sized to allow inspection of a deliverable volume of medicament within the medicament container, wherein the label is selected such that a size of the at least one cutout or transparent area corresponds to a selected medicament container; and
   applying the label onto the shell to allow inspection of a deliverable volume of medicament within the selected medicament container through the at least one cutout or transparent area,
   wherein selecting the label comprises selecting the label comprising a foil having a first surface and a second surface, wherein the at least one cutout or transparent area is arranged in the foil,
   wherein applying the label comprises arranging an opaque part of the foil relative to the shell such that interior portions of the drug delivery device outside a deliverable volume are obscured,
   wherein the method comprises filling the medicament container with a first deliverable volume that is different from a greater deliverable volume,
   wherein the medicament container is adapted to store the greater deliverable volume, and
   wherein applying the label comprises covering a part of the medicament container that would be necessary to allow inspection of the greater delivery volume with a portion of the opaque part of the foil, wherein the portion of the opaque part of the foil is arranged proximally of the cutout or of the transparent area.

20. A method of delivering a drug from a drug delivery device, the method comprising:
   moving a stopper within a medicament container relative to the medicament container to deliver a dose of the drug from the medicament container,
   wherein the drug delivery device comprises a shell configured to contain one of a plurality of medicament containers prefilled with different deliverable volumes of a medicament, and wherein at least an area of the shell adapted to contain the selected medicament container is transparent,
   wherein the medicament container is arranged within the shell,
   wherein a label is arranged on the shell,
   wherein the label is selected out of a plurality of labels, each one having at least one cutout or transparent area sized to allow inspection of a deliverable volume of medicament within the medicament container,
   wherein the label is selected such that a size of the at least one cutout or transparent area corresponds to the medicament container;
   wherein the plurality of labels comprises differently sized cutouts or differently sized transparent areas, and
   wherein the label is selected dependent on the deliverable volume of medicament within the medicament container.

* * * * *